United States Patent [19]

Liedtke

[11] Patent Number: 5,120,710
[45] Date of Patent: Jun. 9, 1992

[54] ORAL LIPID MEDICINAL COMPOSITION

[75] Inventor: Rainer K. Liedtke, Gruenwald, Fed. Rep. of Germany

[73] Assignee: Pharmed GmbH, Gruenwald, Fed. Rep. of Germany

[21] Appl. No.: 524,787

[22] Filed: May 17, 1990

[30] Foreign Application Priority Data

Jun. 19, 1989 [DE] Fed. Rep. of Germany ....... 3919982

[51] Int. Cl.$^5$ ................... A61K 37/26; A61K 37/00; A61K 31/20
[52] U.S. Cl. ........................................ 514/3; 514/11; 514/18; 514/19; 514/21; 514/558
[58] Field of Search .................... 514/3, 558, 866, 18, 514/19, 21, 11; 424/450

[56] References Cited

U.S. PATENT DOCUMENTS 4,434,159  2/1984  Sekine et al. ........................... 514/3
4,619,794  10/1986  Hauser ................................. 424/450

FOREIGN PATENT DOCUMENTS 0246540  11/1987  European Pat. Off. .
52-57313  5/1977  Japan .
55-17328  2/1980  Japan .

OTHER PUBLICATIONS

*The Merck Index*, Merck & Co., Inc., Rahway, N.J., pp. 137, 138, 249, 559, 789–791, and 1373 (1989).
Chemical Abstracts (93:101480g) 1980.
Chemical Abstracts (87:73384j) 1977.
Chemical Abstracts (108:101382e) 1988.

*Primary Examiner*—Frederick E. Waddell
*Assistant Examiner*—K. Weddington
*Attorney, Agent, or Firm*—Oblon, Spivak, McClelland, Maier & Neustadt

[57] ABSTRACT

To improve the absorption of actve ingredients, which are not adequately bio-available on oral administration, an oral lipid medicinal composition is formed by combining a semi-solid, lipophilic component with a solid, water-soluble component. The semi-solid component is a homogeneous lipid mixture that exists as a hard fat with thermally reversible fat/liquid melting property, at least 95% of which is present in the liquid aggregate state below the body temperature of 37° C. and comprises monoacyl-, diacyl-, and triacylglycerides of saturated vegetable fatty acids with chain lengths ranging from 6 to 18 carbon atoms, preferably comprising a mixture of 40 to 60% monoacyl- and diacylglycerides and 40 to 60% triacylglycerides, in which the active ingredients are either dissolved, suspended or emulsified. The solid component comprises a non-diffusible, water-soluble shell which is not chemically bonded to the lipid compound and envelops the entire lipid compound and is preferably made of gelatin or starch. The use of protease inhibitors in the lipid mixture can improve the permeation conditions for peptides and proteins. The use of highly disperse silicon dioxide can stabilize the suspension formulations. Physical-chemical and biochemical aspects of the oral lipid medicinal form yield improvements for the absorption of drugs that are not adequately bio-available on oral administration.

9 Claims, No Drawings

ORAL LIPID MEDICINAL COMPOSITION

BACKGROUND OF THE INVENTION

1. Field of the Invention

The present invention relates to oral lipid medicinal compositions, which improve the absorption of active ingredients, which are not adequately bio-available on oral administration, and methods for preparing such compositions.

2. Discussion of the Invention

It is well known that on oral administration of oral drugs, that have been available to date, numerous drugs cannot be adequately absorbed. Among others, such drugs include various antibiotics and in particular drugs with a peptide or protein structure. To date, the latter can be effectively applied only parenterally, since following oral administration, they become biochemically inactive already in the gastrointestinal tract, before they even reach the site of absorption. The best known example is the blood sugar reducing proteohormone, insulin.

Especially in the case of rectal and dermal applications, it is well known that carrier substrates, which contain, among other things, different mixtures of lipids, can lead to significant differences in drug absorption. Lipid mixtures of this kind have, as a function of the kind and proportion of added lipids (i.e., esters of glycerin and short, medium, or long chain, saturated or unsaturated fatty acids, which in turn can also be present as monoacylglycerides and monoacidic or mixed acid di- and triacylglycerides), a corresponding different solubility behavior and also different solubility behavior for the active ingredients. Consequently, quantitative and qualitative different relations of lipid mixtures can have a significant impact on drug absorption. In accordance with the resulting hydrophilic/lipophilic ratios, the active ingredients must also be worked into the lipid compounds in a specific pharmaceutical format.

However, rectal and dermal applications do not fulfill the prerequisites of fast bio-availability in all cases, as desired or required by some drugs, due to their specific pharmacokinetic profiles and anatomical peculiarities. Tests to apply oral formulations based exclusively on fats, in particular with triacylglycerides as tablets, compressed fat granules or smaller fat globules (fat pellets) with high melting points in order to attain delayed release through diffusion or enzymatic erosion, have already been known for a long time. However, these formulations require a specific manufacturing technology, are suitable primarily only for lipophilic drugs and exhibit no advantages in bio-availability with respect to the usual oral drug formulations, e.g., hydrophilic tablets. Therefore, they have not found any wide therapeutic use.

Attempts to use so-called liposomes, i.e., preferably with the use of phospholipids, such as, among others, phosphatidylcholine, manufactured smallest spherical lipid particles (nano particles), as a drug-including vehicle, are also known. The manufacture of these particles is technically complicated, and in particular liposomes have significant stability problems.

A commercial alternative is the attempt in the direction of highly disperse particles, containing primarily triacylglyceride particles (micro pellets), which are also present, e.g., as a powder.

Another problem with different fat mixtures is that they can exhibit unstable modifications and thus are sensitive to storage. This applies in particular to fat mixtures, e.g., based on cacao butter. The use of unsaturated fatty acids, such as oleic acid (C18:1), linoleic acid (C18:2) and linolenic acid (C18:3) in fat mixtures can also result in oxidation-induced storage problems with the risk of rancidity. Long chain triacylglycerides also have relatively poor solution and solubility properties and are, therefore, suitable primarily for more lipophilic drugs. In addition, apparently following absorption, they are also transported predominantly over lymphatic paths in the gastrointestines, which is a different pathway for the transport of esters of glycerin and short chain fatty acids. Due to the distinctly lower flux rates in the lymph pathways, this results on the whole in slower absorption. In addition, long chain triacylglycerides of gastrointestinal lipases are hydrolyzed more than medium chain ones.

Thus, there remains a need for improving the absorption of active ingredients, which are not adequately bio-available following oral administration.

SUMMARY OF THE INVENTION

Accordingly, one object of the present invention is to provide medicinal compositions which result in effective absorption of active ingredients, which are not adequately bio-available on oral administration.

It is another object of the present invention to provide a method for preparing medicinal compositions which result in the effective absorption of active ingredients which are not adequately bio-available on oral administration.

These and other objects, which will become apparent during the course of the following detailed description, have been achieved by oral lipid medicinal composition formed by combining a semi-solid, lipophilic component with a solid, water-soluble component, wherein the semi-solid component is a homogeneous lipid mixture that exists as a hard fat with a thermally reversible solid/liquid melting property and at least 95% of which is present in the liquid aggregate state below the body temperature of 37° C, and comprises monoacyl-, diacyl- and triacylglycerides of saturated vegetable fatty acids with chain lengths ranging from 6 to 18 carbon atoms, preferably comprising a mixture of 40 to 60% monoacyl- and diacylglycerides and 40 to 60% triacylglycerides, in which the active ingredients are either dissolved, suspended or emulsified, and wherein the solid component of the medicinal form comprises a non-diffusible, water-soluble shell that envelops the entire lipid compound, is not chemically bounded to the lipid compound, and is made of a hard or soft gelatin or starch, and can also contain a protective layer against the gastric juice, and a method for preparing such compositions in which the heated liquid active ingredient-containing lipid is poured into a prefabricated shell.

DETAILED DESCRIPTION OF THE PREFERRED EMBODIMENTS

Thus, at least 95% by weight of the lipid compound is present in the liquid aggregate state at the physiological human body temperature of 37° C.

In one embodiment of the invention to further optimize the proportions of fatty acids in the lipid mixture, the ratio of fatty acids that are used in the entire lipid mixture amounts to 10–18% for caprylic acid, 5–15% for capric acid, 45–55% for lauric acid, 9–15% for myristic acid, 3–10% for palmitic acid, and 3–10% for stearic acid, and these fatty acids are present as components of monoacyl-, diacyl- and triacylglycerides.

An example of a mixture for such a lipid formulation, which serves only as further explanation of the invention without restricting it thereto is a composition in which the percentages of the fatty acids added are: 16% caprylic acid, 13% capric acid, 50% lauric acid, 11% myristic acid, 5% palmitic acid and 5% stearic acid, and the percentages of the mono-, di-, and triacylglycerides are monoacylglyceride: 34%; diacylglyceride: 14%; and triacylglyceride: 52%. The fatty acids in the lipid mixture are determined by gas chromatography (GC) by means of the fatty acid methyl esters. Acetylation of the lipid compound leads to glycerides, which can then be directly introduced to the gas chromatograph. The evaluation of the peak of the gas chromatography yields a quantitative picture of the obtained monoacyl-, diacyl- and triacylglycerides, wherein the partial glycerides exhibit acetyl groups.

The proof of the suitable melting behavior of this lipid compound can be determined either by determining the rising melting point, the dropping point or by means of thermoanalysis. In this case, thermoanalysis reproduces the entire melting pattern during the absorption of heat. With thermoanalysis it can be proven with a lipid composition of the aforementioned kind that at approximately 24° C. only a very small portion of the lipid compound is melted, that the bulk of the melting process is at 30° C. and only a small portion melts at 37° C. In contrast, the measurement conducted by comparison of the rising melting point alone shows a value of approximately 36° C. A suitable solid fat index (solid fat content, SFC) for a lipid compound compounded in such a manner can be determined by means of nuclear magnetic resonance measurement. In this manner the particles, which are still solid at specific temperatures, are measured. For example, the lipids in a precision pre-treatment are treated as follows: 3 g of a specimen are melted for 30 minutes at 70°, stored for 60 minutes at 0° C. and stored for 35 minutes at measurement temperature. A characteristic pattern of the mean value of the solid content resulting from 3 measurements is, for example, for the aforementioned exemplary lipid formulation: 0° = 83%, 10° C. = 79%, 20° C - 63%, 25° C. = 45%, 30° C. = 13%, 32.5° C. = 6%, 35° C. =4%, 37.5° C. = 2%, 40C. = 0%. Therefore, at a temperature of 35° C., 96% of the lipid mixture is almost completely in the liquid state and at 37.5° C., 98% is almost completely in the liquid state, whereas at the normal external storage temperatures said lipid mixture shows physically no fluid properties.

In order to improve the absorption especially of substances with a peptide or protein structure, protease inhibitors, in particular aprotinin, are added, according to another embodiment of the invention, to the lipid compound as another protective substance.

In order to stabilize suspended active ingredients in the lipid composition, in another embodiment of the invention, 1-5% of highly disperse silicon dioxide in the hydrophilic or hydrophobic form is added.

According to another embodiment of the invention, to simplify the commercial manufacturing process, the heated and liquid active ingredient-containing lipid compound is poured directly into prefabricated capsules made of hard or soft gelatin and solidified therein.

To improve the therapy with drugs that to date have been administered primarily only parenterally, especially drugs with a peptide or protein structure such as insulin, calcitonin, atrial natriuretic peptide (ANP), interferon, somatostatin, and encephaline are added, in another embodiment of the invention.

To improve the therapy of drugs which to date have been administered parenterally or were not satisfactorily absorbed when taken orally, antibiotics, in particular cephalosporins, are added according to another embodiment of the invention.

To improve drug therapy by reducing the required dose, thus reducing the potential for side effects, cardiovascularly effective substances such as beta blockers, calcium antagonists and diuretics such as steroid hormones such as estradiol, progesterone, testosterone and cortisol are added in accordance with another embodiment of the invention.

The advantages of the invention result from the fact that the lipid mixture is a thermally reversible solid-fluid system with natural permeation promoting properties, wherein the specific composition of the lipids has good absorptive capacity for both hydrophilic and lipophilic active ingredients. Thus, no additional penetration promoters, so-called chemical enhancers, are required. This also excludes the risk of incompatibility and local damage to the mucus membrane, which can accompany the use of enhancers.

The good hydrophilic-lipophilic ratios also avoid the use of additional ionogenic or non-ionogenic emulsifiers, surfactants or solubility promoters such as polyethylene glycol compounds (PEG). A physiological emulsification of the lipids released in the gastrointestinal tract occurs due to the endogenic bile acids.

The lipid formulations exhibit excellent compatibility and the starting substances originate from natural sources such as coconut and palm seed fats. The lipid mixtures also meet the USP XXI/National Formulary NF XVI, 4th supplement of the monograph for "Hard Fat".

In a test of a lipid formulation compounded in the above described manner for acute oral toxicity ($LD_{50}$, according to OECD no. 401) on rats, the acute mean oral $LD_{50}$ was over 2,000 mg/kg of body weight of the rat (limit test). In testing the contact sensitization of the test model according to Magnusson & Kligman (according to OECD no. 406) the sensitization test yielded for the same lipid compound =0% (0/20) and was classified as non-irritating and non-sensitizing on the skin of a guinea pig. An acute dermal toxicity on rats (according to OECD no 402) yielded a mean $LD_{50}$ dermally over 2,000 mg/kg of body weight (limit test).

Since the lipid formulations contain exclusively saturated fatty acids, they also exhibit good stability during storage with respect to atmospheric oxygen and thus are not subject to the risk of becoming rancid. The solid shell represents another protective measure against oxidation.

Since the active ingredient-containing lipid mixtures exist in the liquid aggregate state in the gastrointestinal tract at body temperature, as confirmed by means of the aforementioned analysis through thermoanalysis, rising melting point and solid fat index, following the rapid exit from the carrier shell they spread out directly on the mucus membrane. The result is also good concentration gradients, since the lipids are only partially water soluble and can hardly be diluted. This also enhances rapid absorption and the exposure period for inactivation by means of the gastrointestinal lipases and proteases is shortened.

On the other hand, the solid state of the lipid mixture during storage improves the stability of the active ingredients, and pharmaceutical processing formats such as suspensions or emulsions are mechanically stabilized through solidification.

Both the technological processing of the lipid compounds and the introduction of the lipid compound into the solid shell can be performed with the conventional pharmaceutical methods and facilitate economic mass production.

The lipid mixtures used in the oral lipid medicinal preparation also enhance the efficacy of active ingredients with a peptide and protein structure, which to date could be applied only parenterally, in the form of injections. The therapeutic use by administering corresponding active substances to patients in oral form, instead of in injection form, is offered by the present invention. The fact that it is, as a general rule, possible to produce biological effects also via the oral administration route by means of lipid formulation, e.g., for blood sugar-lowering proteohormone insulin, is demonstrated by the following Examples, which serve only to further explain the invention without restricting it to said Examples.

EXAMPLES

EXAMPLE 1

Insulin was administered perorally to healthy, non-conditioned white mice. To this end, aqueous insulin solutions with insulin concentrations of 100 IU/ml were dispersed at 38° C. in a lipid mixture of the above compounded kind (percentages of the fatty acids: 16% caprylic acid; 13% capric acid; 50% lauric acid; 11% myristic acid; 5% palmitic acid; and 5% stearic acid and percentages of the mono-, di-, and triacylglycerides: 34% monoacylglyceride; 14% diacylglycerides; and 52% triacylglyceride), which was treated with an addition of 3% highly disperse silicon dioxide, emulsified for several minutes with ultrasonics and then hardened. Microscopic rechecking in the smear preparation of the lipid compound and in aqueous suspension preparations that have been dyed twice shows spherical-vesicular complexes of water and oil or complexes of water and oil and water in the aqueous preparation.

Following reheating to 38° C, 0.4ml of the lipid mixtures with varying insulin concentrations, between 9.5 IU and 0.7 IU insulin/kg of body weight, were injected into the stomachs of groups of 3 fasting mice with a peroral plastic catheter. The individual doses were delivered by diluting the insulin starting solutions, through the corresponding addition of another lipid solution. For each active substance group there was a simultaneous separate and equally large control group to which the same volume of insulin-free lipid mixture was administered. Blood was sampled before and 1, 2 and 4 hours following administration through the caudal vein. The blood glucose concentrations were determined by means of reflection densitometry from the whole blood. The results are shown in Table I.

TABLE I

| Insulin dosage (IU/kg of body weight) | Time (hours after administration) | Control Group (only lipid) blood glucose (mg/dl) (mean value ± standard deviation) | Active Group (lipid + insulin) |
|---|---|---|---|
| 9.5 | 0 | 165 ± 8 | 145 ± 6 |
|  | 1 | 168 ± 15 | 26 ± 13 |
|  | 2 | 176 ± 2 | 21 ± 2 |

TABLE I-continued

| Insulin dosage (IU/kg of body weight) | Time (hours after administration) | Control Group (only lipid) blood glucose (mg/dl) (mean value ± standard deviation) | Active Group (lipid + insulin) |
|---|---|---|---|
|  | 4 | 136 ± 21 | 24 ± 7 |
| 1.9 | 0 | 80 ± 2 | 82 ± 10 |
|  | 1 | 103 ± 12 | 45 ± 2 |
|  | 2 | 97 ± 10 | 67 ± 15 |
|  | 4 | 77 ± 5 | 62 ± 14 |
| 0.95 | 0 | 136 ± 14 | 121 ± 20 |
|  | 1 | 147 ± 19 | 82 ± 9 |
|  | 2 | 137 ± 10 | 99 ± 21 |
|  | 4 | 121 ± 22 | 122 ± 9 |
| 0.7 | 0 | 116 ± 10 | 123 ± 9 |
|  | 1 | 109 ± 9 | 104 ± 9 |
|  | 2 | 108 ± 3 | 84 ± 29 |
|  | 4 | 107 ± 17 | 107 ± 40 |

The peroral application of insulin resulted, both with respect to the values of the control group that were the same over time and the starting values of the active groups, in a significant, reproducible and dosage-dependent lowering of the blood glucose. With orally administered, unmodified, aqueous insulin solutions no corresponding blood sugar-lowering effect could be detected.

EXAMPLE 2

In a human pharmacological test 9 healthy, male subjects received either subtherapeutic insulin doses (regular human insulin), on average 0.2 or 0.4 IU/kg of body weight, or the same lipid formulation without insulin (placebo) orally. To this end, the same hardened insulin lipid emulsion prepared in Example 1 was in hard gelatin capsules. Three subjects each received 16 IU insulin (8 IU/capsules) or 32 IU and 3 subjects received capsules with placebos. All subjects fasted overnight and received, one hour after administration of the capsules, in periods of one hours, 20 g of standardized carbohydrates. The serum insulin concentration was determined by means of radio immunoassay. The results are shown in Table II.

TABLE II

| | Hours After Administration | | | | | |
|---|---|---|---|---|---|---|
| | 0 | 0.5 | 1 | 2 | 3 | 4 | 6 |
| | mean values of insulin in serum ($\mu$U/ml) | | | | | |
| placebo | 4.8 | 5.3 | 5.3 | 6.9 | 7.1 | 7.1 | 4.7 |
| 16 IU | 5.8 | 5.8 | 6.1 | 8.6 | 9.6 | 8.5 | 6.8 |
| 32 IU | 6.1 | 6.3 | 7.0 | 8.8 | 8.1 | 13.6 | 9.8 |

It is evident from a group comparison of the chronological patterns of the mean insulin serum concentration that the groups with the insulin formulation exhibit higher insulin concentrations than the placebo group and also the two insulin dosages show differences among one another. It can be inferred that the insulin is absorbed in the intestinal tract of these healthy and normally counter-regulating subjects.

It is evident from the two aforementioned Examples that with the subject matter of the invention, even with molecules having a peptide character, which are usually biologically inactivated in the gastrointestinal tract, biological effects can be generated with an oral application.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the U.S. is:

1. An oral lipid medicinal composition, comprising a semi-solid, lipophilic component and a solid, water-soluble component, wherein said semi-solid component is a homogeneous lipid mixture that exists as a hard fat with a thermally reversible solid/liquid melting property, and at least 95% of which is present in the liquid aggregate state below the body temperature of 37° C., and comprises monoacyl-, diacyl-, and triacylglycerides of saturated vegetable fatty acids with chain lengths ranging from 6 to 18 carbon atoms, in which a protease inhibitor and an effective amount of an active ingredient which has a peptide or protein structure are either dissolved, suspended or emulsified, and wherein said solid component comprises a non-diffusible, water-soluble shell that envelops the entire semi-solid component, is not chemically bonded to the semi-solid component, and is made of a hard or soft gelatin or starch.

2. The composition of claim 1, wherein said active ingredient is insulin.

3. The composition of claim 1, wherein said semi-solid component comprises 40 to 60% monoacylglycerides and diacylglycerides and 40 to 60% triacylglycerides.

4. The composition of claim 1, wherein said water-soluble shell further contains a protective layer against gastric juice.

5. The composition of claim 1, wherein the percentages of fatty acids that are contained in the entire lipid mixture are 10–18% for caprylic acid, 5–15% for capric acid, 45–55% for lauric acid, 9–15% for myristic acid, 3–10% for palmitic acid, and 3–10% for stearic acid, and said fatty acids are present as components of monoacyl-, diacyl- or triacylglycerides.

6. The composition of claim 1, wherein said protease inhibitor is aprotinin.

7. The composition of claim 1, wherein 1-5% of highly disperse silicon dioxide in hydrophilic or hydrophobic form is added to said lipid compound.

8. The composition of claim 1, wherein said active ingredient is selected from the group consisting of insulin, calcitonin, atrial natriuretic peptide (ANP), interferon, somatostatin, and enkephalin.

9. The composition of claim 1, wherein 95% of said lipid mixture is present in the liquid aggregate state at the physiological human body temperature of 37° C.

* * * * *